United States Patent [19]
Cabrera et al.

[11] Patent Number: 5,525,729
[45] Date of Patent: Jun. 11, 1996

[54] BENZ-1,2,3-OXATHIAZIN-4(3F)-ONE-2,2-DIOXIDES, A PROCESS FOR THEIR PREPARATION AND THEIR USE AS ELECTROPHILIC FLUORINATING AGENTS

[75] Inventors: Ivan Cabrera, Dreieichenhain; Wolfgang Appel, Kelkheim, both of Germany

[73] Assignee: Hoechst Aktiengesellschaft, Germany

[21] Appl. No.: 402,914

[22] Filed: Mar. 13, 1995

[30] Foreign Application Priority Data

Mar. 15, 1994 [DE] Germany .................. 44 08 681.4

[51] Int. Cl.⁶ .................................. C07D 291/00
[52] U.S. Cl. ........................................... 544/2
[58] Field of Search ................................. 544/2

[56] References Cited

U.S. PATENT DOCUMENTS

| | | | |
|---|---|---|---|
| 3,780,030 | 12/1973 | Morris | 260/243 R |
| 3,926,976 | 12/1975 | Clauss et al. | 260/243 R |
| 4,018,920 | 4/1977 | Chan | 424/246 |
| 4,479,901 | 10/1984 | Barnette | 260/239 |
| 4,828,764 | 5/1989 | DesMarteau | 260/397.45 |
| 4,900,867 | 2/1990 | Wilkes et al. | 564/91 |
| 5,003,074 | 3/1991 | Allmendinger et al. | 548/206 |
| 5,086,178 | 2/1992 | Banks | 544/351 |
| 5,227,493 | 7/1993 | Banks | 564/307 |
| 5,254,732 | 10/1993 | Differding | 564/82 |

FOREIGN PATENT DOCUMENTS

| | | |
|---|---|---|
| 0211578 | 2/1987 | European Pat. Off. . |
| 3623184 | 1/1988 | Germany . |

OTHER PUBLICATIONS

Tetrahedron Letters, vol. 29, No. 29, No. 47, pp. 6087–6090, 1988.

Furin G. G., entitled "2. Some Electrophilic Fluorination Agents". In: New Fluorinating Agents in Organic Synthesis, pp. 35–68.

Journal of Synthetic Chemistry, Japan, vol. 50, No. 4, Apr. 1992, pp. 338–346 by Teruo Umemoto entitled "Recent Development of Fluorinating Agents".

The Journal of Organic Chemistry, vol. 57, No. 15, Jul. 17, 1992 by Resanti G & DesMarteau entitled "Electrophilic Fluorination of Pharmacologically Active 1,3–Dicarbonyl Compounds", pp. 4281–4284.

Angewandte Chemie, vol. 85, No. 22, Nov. 1973 entitled "Oxathiazinondioxide, eine neue Gruppe von Susstoffen" by Clauss et al., pp. 965–973.

Journal of Org. Chem., vol. 48, (1983), pp. 761–762.
Tetrahedron Letter, vol. 29, (1988), pp. 6087–6090.
Journal Chem. Soc. Perkin, Tans I, (1988), pp. 2805–2811.
Journal Am. Chem. Soc., vol. 1212 (1990), pp. 8563–8575.

*Primary Examiner*—Cecilia Tsang
*Assistant Examiner*—King Lit Wong
*Attorney, Agent, or Firm*—Curtis Morris & Safford

[57] ABSTRACT

The invention relates to compounds of the formula (I)

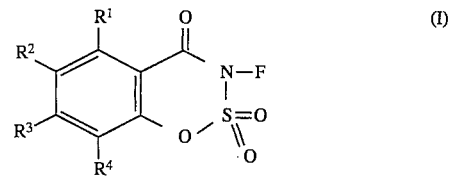

where $R^1$, $R^2$, $R^3$ and $R^4$ are, independently of one another, hydrogen, $CF_3$, $NO_2$, $CN$, halogen, $-S(NSO_2CF_3)CF_3$, $(C_1-C_4)$-alkyl, phenyl, $SO_2R^5$, $COOR^5$, $NR_2^5$, where $R^5$ is $(C_1-C_4)$-alkyl, which can also be fluorinated, or phenyl, or $R^1$ and $R^2$, $R^2$ and $R^3$ or $R^3$ and $R^4$ together form an aliphatic or aromatic ring which can also contain an oxygen, sulfur or nitrogen atom.

The invention further provides a process for preparing the compounds of the formula (I), which comprises reacting compounds of the formula (II)

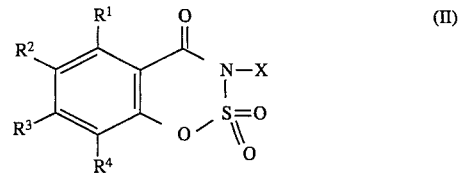

where $R^1$ to $R^4$ are as defined above and X is hydrogen or an alkali metal, with elemental fluorine in the presence of an inert solvent and, if desired, an alkali metal fluoride at low temperatures.

The invention further provides for the use of the compounds of the formula (I) for the fluorination of compounds having carbanion character.

6 Claims, No Drawings

BENZ-1,2,3-OXATHIAZIN-4(3F)-ONE-2,2-DIOXIDES, A PROCESS FOR THEIR PREPARATION AND THEIR USE AS ELECTROPHILIC FLUORINATING AGENTS

The invention relates to benz-1,2,3-oxathiazin-4(3F)-one-2,2-dioxides, a process for their preparation and their use as electrophilic fluorinating agents.

Many new agricultural and pharmaceutical active ingredients contain F atoms at strategic positions. A reason for this is the fact that the replacement of hydrogen by fluorine (isosteric substitution) or of hydroxyl groups by fluorine (isopolar substitution) very often leads to an improvement in the activity. The selective introduction of fluorine into organic molecules has therefore become a very important task in modern chemistry. Although the introduction of diethylaminosulfur trifluoride and other reagents in this class of compounds has achieved a breakthrough in the field of nucleophilic fluorination, there is a further need for safe, mild and efficient electrophilic fluorinating agents. Most of such electrophilic reagents, such as perchloryl fluoride, trifluoromethyl hypofluoride, $CsSO_4F$, etc, are toxic and very aggressive chemicals with which explosions are not infrequently observed. Furthermore, the storage stability of such materials is very limited. "$F^\oplus$" reagents based on N-F-containing compounds have been investigated very intensively, since some of these materials have proven to be readily isolable, storage-stable and efficient fluorinating agents. The first experiments in this direction were carried out using perfluoro-N-fluoropiperidine (A) (J. Chem. Soc. Perkin Trans. I 1988, 2805). However, owing to the complicated synthesis (yield max. 13%) and the side reaction during fluorination, this compound is not of interest for practical purposes. Other known N-F fluorinating agents are N-fluoropyridin-2-(1H)one (B) (J. Org. Chem. 1983, 43, 761), N-fluorosulfonamides (C) (U.S. Pat. Nos. 4,479,901, 4,828,764, DE 36 23 184 A); camphor N-fluorosultam (D) (Tetrahedron Lett. 1988, 29, 6087); N-fluoroquinicludinium salts (E) (J. Chem. Soc. Perkin Trans I, 1988, 2805); N-fluoropyridiniumsalts (F) (J. Am. Chem. Soc. 1990, 112, 8563); N-fluoro-N-perfluoromethyl sulfonamides (G) (U.S. Pat. 4,828,764, U.S. Pat. No. 5,227,493) and N-fluoro-N-chloromethyltriethylenediamine bis(tetrafluoroborate) (F-Teda (H)) (U.S. Pat. No. 5,086,178).

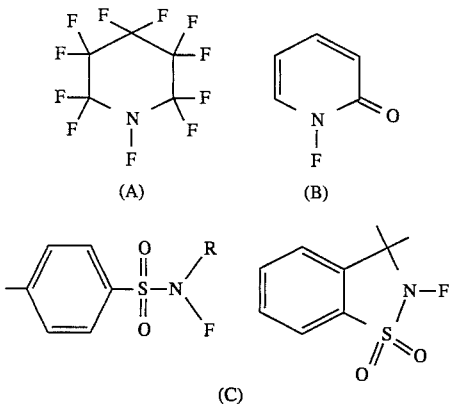

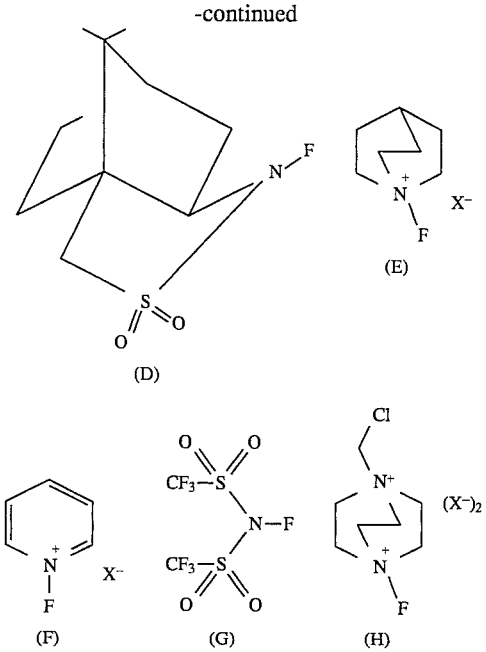

The compound (B) is not storage stable. The reagent (G), which is the strongest known NF compound, requires a very complicated synthesis for its preparation. The compounds (C), (F) and (H) are commercially available. However, the commercially available N-fluorosulfonamides have the disadvantage that, because of the hydrogen atom in the a position of the N-alkyl radical, an HF elimination can very easily occur as a side reaction. In the case of N-alkyl radicals which possess no hydrogen atoms in the a position., e.g. a t-butyl group, the yield in the preparation of the NF compound is very small. Although the charged systems (H), (F) are very efficient fluorinating agents, a decisive disadvantage of these systems is their limited solubility in the usual organic solvents. F-Teda (H) additionally has the disadvantage that a Hofmann elimination often takes place in the case of this quaternary ammonium salt. This is a particular problem in the fluorination of strong carbanions.

There is therefore a great need for an electrophilic fluorinating agent which does not have the disadvantages described, can be easily prepared from readily available starting materials and possesses a high storage stability.

This object is achieved by compounds of the formula (I)

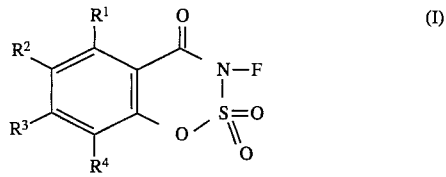

where $R^1$, $R^2$, $R^3$ and $R^4$ are, independently of one another, hydrogen, $CF_3$, $NO_2$, CN, halogen, —S ($NSO_2CF_3$)$CF_3$, $(C_1-C_4)$-alkyl, phenyl, $SO_2R^5$, $COOR^5$, $NR_2^5$, where $R^5$ is $(C_1-C_4)$-alkyl which can also be fluorinated, or phenyl, or $R^1$ and $R^2$, $R^2$ and $R^3$ or $R^3$ and $R^4$ together form an aliphatic or aromatic ring which can also contain an oxygen, sulfur or nitrogen atom.

In many cases, compounds of the formula (I) which are of interest are those in which $R^1$, $R^2$, $R^3$ and $R^4$ are, independently of one another, hydrogen, $NO_2$, CN, $CF_3$, $SO_2R^5$, $S(NSO_2CF_3)CF_3$.

Compounds which are of particular importance here are the disubstituted and monosubstituted compounds, i.e. compounds of the formula (I) in which 2 or 3 of the radicals $R^1$, $R^2$, $R^3$ and $R^4$ are hydrogen.

Particular importance is also attached to the compounds of the formula (I) where $R^1$ and $R^2$ or $R^2$ and $R^3$ or $R^3$ and $R^4$ form a phenyl or cyclohexyl ring.

Naturally, the unsubstituted compound, benz-1,2,3-oxathiazin-4(3F)-one-2,2-dioxide is also of particular interest.

Depending on the pattern of substitution and on the solvent, it is also possible for the compounds of the formula (I) to be in tautomeric equilibrium with the compounds of the formula (I'):

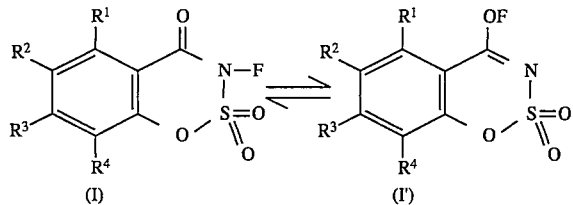

The invention further provides a process for preparing the compounds of the formula (I). It comprises reacting compounds of the formula (II) (prepared as described in Angew. Chem. 85, 965 (1973)), where $R^1$, $R^2$, $R^3$ and $R^4$ are as defined above and X is hydrogen or an alkali metal, with elemental fluorine in the presence of an inert solvent and, if desired, an alkali metal fluoride at low temperatures.

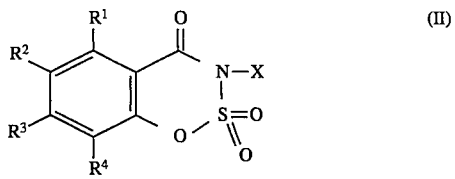

Good results are obtained, for example, if X is hydrogen, sodium or potassium.

Alkali metal fluorides which have been found to be useful are sodium or potassium fluoride, in particular sodium fluoride.

The fluorinating agent fluorine is advantageously used in admixture with inert gas such as nitrogen, $SF_6$, $CF_4$ or noble gases such as helium, neon, argon, krypton. The preferred inert gas is nitrogen. For the fluorination, it is possible to use fluorine/inert gas mixtures containing up to 30% by volume of fluorine.

In many cases, it has also been found to be useful to carry out the fluorination using an $N_2/F_2$ mixture containing between 1 and 15% by volume, in particular between 2 and 10% by volume, preferably from 3 to 6% by volume, of $F_2$.

Suitable solvents are, for example, halogenated hydrocarbons such as dichloromethane, chloroform, carbon tetrachloride, fluorotrichloromethane, trifluorotrichloroethane, tetrafluorodichloroethane or nitriles, in particular acetonitrile.

The temperature at which the reaction is carried out can be varied within a wide range and is in particular in the range from '10° to −80° C. The selection of the temperature depends in the individual case on the selection of the reaction conditions such as fluorine concentration, composition of the solvent mixture, etc. The fluorination is advantageously carried out at temperatures of from −80° to −20° C., in particular from −60° to −30° C., preferably from −50° to −35° C.

The invention further provides for the use of the compounds of the formula (I) for the fluorination of compounds possessing open or concealed carbanion character, such as 1,3-dicarbonyl compounds. These compounds can be reacted in very high yields to give the fluorine compounds.

An overview of such reactions is shown in Table 1.

TABLE 1

| Ex. | Starting Material | Product | Yield (%) |
|---|---|---|---|
| 2 | | | 77 |
| 3 | | | 78 |
| 4 | | | 86 |
| 5 | | | 65 |

TABLE 1-continued

| Ex. | Starting Material | Product | Yield (%) |
|---|---|---|---|
| 6 | 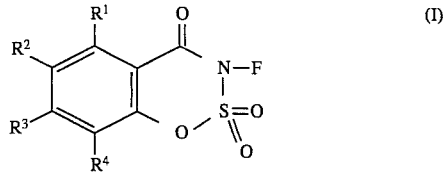 | | 70 |

The compounds of the formula (I) are able to produce iodine if they are treated with sodium iodide solution. The concentration of the compounds can therefore be determined by means of titration.

A further substantial advantage of the new compounds is based on their solubility properties: while the NF compounds are readily soluble in organic solvents, the starting materials are water-soluble. This means that the N-X compounds formed after a fluorination reaction can be readily removed from the reaction medium using water. This results in a simple isolation of the desired fluorinated products. Furthermore, a simple recycling of the materials described here is therefore possible, since the N-X compounds are the starting materials for the preparation of the NF compounds.

EXAMPLE 1

Preparation of benz-1,2,3-oxathiazin-4(3F)-one-2,2-dioxide

In the completely dry (flamed out) fluorination apparatus under $N_2$, 0.98 g (4.4 mmol) of 1,2,3-benz-oxathiazin-4(3H)-one-2,2-dioxide sodium salt are suspended in 120 ml of acetonitrile which has been dried using $CaH_2$, admixed with 0.20 g of NaF and fluorinated at −40° C. using a mixture of 5% (v/v) $F_2$ in $N_2$. Flushing with $N_2$ is subsequently carried out for 0.5 hours at −40° C. and 1 hour at room temperature. The mixture is filtered and the filtrate is quickly distilled in an oil pump vacuum. The white-yellowish solid is taken up in dried ether, clarified by filtration and evaporated on a rotary evaporator. The material can be further purified by precipitation from ether solution using pentane (pure grade). Crystalline benz-1,2,3-oxathiazin-4(3F)-one-2,2-dioxide is filtered off and washed with pentane. After drying in an oil pump vacuum, 0.85 g of benz-1,2,3 -oxathiazin-4(3F)-one-2,2-dioxide (88% of theory based on 11b) is obtained. Mp. from 52° to 53° C. 1H-NMR (300 MHz, $CDCl_3$): δ (ppm) 7.42 (dd, 1 H), 7.59 (dt, 1H), 7.85 (dt, 1H), 8.23 (dd, 1H).

Examples of the compounds which were prepared using benz-1,2,3-oxathiazin-4(3F)-one-2,2-dioxide are summarized in Table 1. The synthesis for Example 2 is described below. The remaining compounds are obtained in a similar manner.

EXAMPLE 2

Ethyl cyclopentanone-2-fluoro-2-carboxylate

A solution of 187 mg (1.2 mmol) of ethyl cyclopentanone-2-carboxylate in 50 ml of dried THF is added at 0° C. under $N_2$ to a suspension of 36 mg of NaH (in 10 ml of THF). The mixture is stirred for 0.5 hours at 0° C. and for 1 hour at room temperature, before the fluorinating agent benz-1,2,3-oxathiazin-4(3F)-one-2,2-dioxide (302 mg, 1.3 mmol in 10 ml of THF) is added. The reaction mixture is stirred for 1 hour at room temperature. The solvent is taken off on a rotary evaporator and the residue is taken up in ether, clarified by filtration and the filtrate is shaken out with water, saturated $NaHCO_3$ solution and water. The ether phase is then dried with $Na_2SO_4$, filtered off and the solvent is removed under reduced pressure. Yield: 161 mg (77% of theory).

We claim:

1. A compound of the formula (I)

(I)

where $R^1$, $R^2$, $R^3$ and $R^4$ are, independently of one another, hydrogen, $CF_3$, $NO_2$, CN, halogen, $—S(NSO_2CF_3)CF_3$, $(C_1–C_4)$-alkyl, phenyl, $SO_2R^5$, $COOR^5$, $NR_2^5$, where $R^5$ is $(C_1–C_4)$-alkyl, which can also be fluorinated, or phenyl, or $R^1$ and $R^2$, $R^2$ and $R^3$ or $R^3$ and $R^4$ together form an aliphatic or aromatic ring which can also contain an oxygen, sulfur or nitrogen atom.

2. A compound of the formula (I) as claimed in claim 1, where $R^1$, $R^2$, $R^3$ and $R^4$ are, independently of one another, hydrogen, $NO_2$, CN, $CF_3$, $SO_2R^5$, or $S(NSO_2CF_3)CF_3$.

3. A compound as claimed in claim 1, where 2 of the radicals $R^1$, $R^2$, $R^3$, $R^4$ are hydrogen.

4. A compound as claimed in claim 1, where 3 of the radicals $R^1$, $R^2$, $R^3$, $R^4$ are hydrogen.

5. A compound of the formula (I) as claimed in claim 1, where $R^1$ and $R^2$ or $R^2$ and $R^3$ or $R^3$ and $R^4$ form a phenyl or cyclohexyl ring.

6. Benz-1,2,3-oxathiazin-4(3F)-one-2,2-dioxide.

* * * * *